(12) United States Patent
Nissilä et al.

(10) Patent No.: US 6,277,080 B1
(45) Date of Patent: Aug. 21, 2001

(54) METHOD AND APPARATUS FOR MEASURING EXERTION ENDURANCE

(75) Inventors: Seppo Nissilä; Juha Röning; Antti Ruha; Kauko Väinämö, all of Oulu (FI)

(73) Assignee: Polar Electro Oy, Kemple (FI)

( * ) Notice: Subject to any disclaimer, the term of this patent is extended or adjusted under 35 U.S.C. 154(b) by 0 days.

(21) Appl. No.: 09/142,444
(22) PCT Filed: Mar. 12, 1997
(86) PCT No.: PCT/FI97/00163
§ 371 Date: Nov. 20, 1998
§ 102(e) Date: Nov. 20, 1998
(87) PCT Pub. No.: WO97/33512
PCT Pub. Date: Sep. 18, 1997
(51) Int. Cl.⁷ .................................................. A61B 5/02
(52) U.S. Cl. ........................ 600/508; 600/484; 128/925
(58) Field of Search ................................. 600/481, 483, 600/484, 508, 520, 513; 128/920, 923–925

(56) References Cited

U.S. PATENT DOCUMENTS

| | | | |
|---|---|---|---|
| 4,566,461 | * 1/1986 | Lubell et al. | 600/520 |
| 5,251,626 | 10/1993 | Nickolls et al. | |
| 5,280,792 | 1/1994 | Leong et al. | |

FOREIGN PATENT DOCUMENTS

| | | |
|---|---|---|
| 39 20 526 A1 | 1/1991 | (DE). |
| 39 22 026 A1 | 1/1991 | (DE). |
| 43 38 958 A1 | 5/1994 | (DE). |
| 43 07 545 A1 | 9/1994 | (DE). |
| 0 650 742 A1 | 5/1995 | (DE). |
| WO 92/03094 | 3/1992 | (FR). |

\* cited by examiner

Primary Examiner—George R. Evanisko
(74) Attorney, Agent, or Firm—Hoffman & Baron, LLP

(57) ABSTRACT

The present invention relates to a method and an apparatus for measuring exercise condition, especially a method for measuring an exertion endurance indicator representing exercise condition of a subject to be measured, such as maximal oxygen uptake or any such exertion endurance indicator representing exercise condition. The method is characterized in that, in the method a predetermined calculation formula is used preferably by means of a neural network, to which formula physiological parameters representing the subject to be measured are supplied. The input parameters comprise at least one or more of the following physiological parameters, such as sex, age, height, weight. One or more output parameters representing the exertion endurance indicator representing the exercise condition of the subject to be measured are obtained as a result from the calculation formula. In addition to the physiological parameters, one or more resting heartbeat parameters measured specifically from resting heartbeat are used as input parameters of the calculation formula. In the preferred embodiment of the invention, the calculation formula is formed by means of a neural network construction.

29 Claims, 3 Drawing Sheets

$a1 = F_1(W1*p + b1)$   $a2 = F_2(W2*a1 + b2)$   $a2 = F_2(W2*F_1(W1*p + b1) + b2)$

VR = length of input vector
S1 = number of neurons in hidden layer
S2 = number of neurons in output layer
$F_n$ = activation function W1 = first weighting coefficient matrix
W2 = second layer weighting coefficient matrix
b1 = first bias vector
b2 = second layer bias vector
p = features, i.e. input parameters

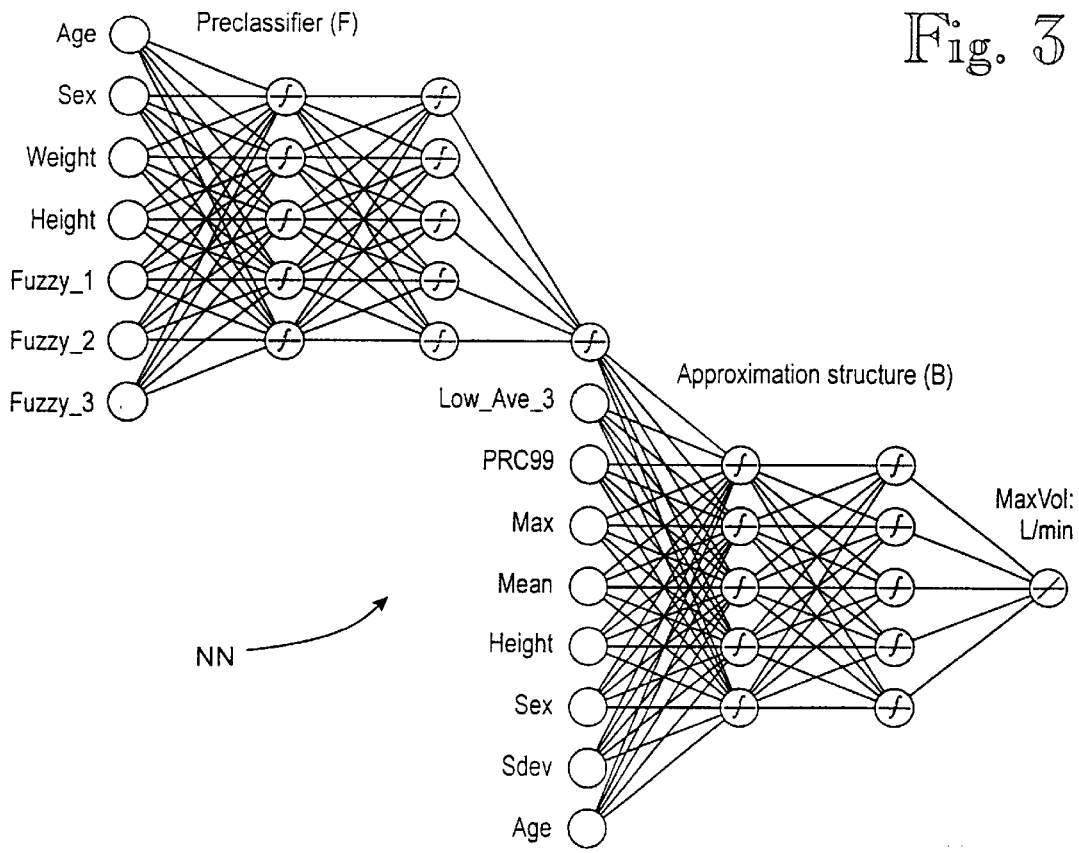

$$Fw1 = \begin{bmatrix} -0,7 & 1,9 & 3,3 & 1,9 & -2,3 & -2,4 & -4,2 \\ -1,2 & -1,2 & -1,2 & 0,5 & 4,0 & 0,5 & -2,1 \\ -0,9 & -0,3 & -1,5 & 0,7 & 0,4 & -1,4 & 0,2 \\ -3,2 & 0,4 & -2,8 & 0,7 & 1,4 & -1,9 & 0,3 \\ 1,9 & -2,2 & -0,6 & 0,6 & -1,1 & 1,1 & -5,1 \end{bmatrix} \quad Fw2 = \begin{bmatrix} 0,9 & 0,7 & -1,5 & -1,8 & -0,4 \\ 0,0 & 4,0 & -7,0 & 0,2 & -2,9 \\ 1,5 & -1,9 & -2,8 & 3,2 & 2,6 \\ -1,6 & 0,4 & -1,0 & 2,6 & -0,1 \\ 1,7 & -0,5 & 0,6 & -0,2 & 0,2 \end{bmatrix}$$

$$Bw1 = \begin{bmatrix} 1,5 & -0,5 & 0,6 & -0,5 & 0,7 & -0,3 & 0,0 & -0,3 & 0,2 \\ 2,4 & -7,2 & 0,9 & -5,3 & 6,6 & 2,0 & -1,8 & 3,4 & -0,2 \\ 1,0 & -7,0 & 2,0 & -0,7 & 0,0 & -1,8 & -0,6 & 2,8 & -2,6 \\ 1,3 & 3,7 & -3,6 & -3,3 & 2,5 & 3,2 & -1,8 & 1,2 & 0,9 \\ 2,3 & -1,0 & 0,8 & -5,0 & 4,6 & 1,5 & -2,6 & 2,6 & 2,6 \end{bmatrix} \quad Bw2 = \begin{bmatrix} -0,9 & -0,2 & 0,5 & 0,8 & -0,7 \\ 3,9 & -3,4 & -2,1 & 0,9 & 0,3 \\ 1,1 & -4,8 & 4,0 & 4,8 & -3,5 \\ 0,4 & 0,4 & 0,1 & -1,0 & 2,0 \\ -0,2 & 0,3 & 0,0 & -0,8 & 1,1 \end{bmatrix}$$

Fw3 = (1,7 -0,6 2,8 1,3 1,5)   Bw3 = (-0,8 -0,2 0,3 0,9 -1,8)

$$Fb1 = \begin{bmatrix} 1,0 \\ -0,2 \\ -0,4 \\ -2,8 \\ -0,1 \end{bmatrix} \quad Fb2 = \begin{bmatrix} 0,6 \\ 0,6 \\ -1,4 \\ -0,7 \\ 2,5 \end{bmatrix} \quad Fb3 = 1,4 \quad Bb1 = \begin{bmatrix} 0,0 \\ 0,4 \\ -0,7 \\ 0,7 \\ 1,4 \end{bmatrix} \quad Bb2 = \begin{bmatrix} -0,7 \\ 2,5 \\ -3,9 \\ 0,0 \\ -0,2 \end{bmatrix} \quad Bb3 = -0,4$$

METHOD AND APPARATUS FOR MEASURING EXERTION ENDURANCE

BACKGROUND OF THE INVENTION

1. Field of the Invention

The invention relates to a method for measuring exercise condition, especially to a method for providing an exertion endurance indicator representing an exercise condition of a subject to be measured, such as maximal oxygen uptake or any such exertion endurance indicator representing an exercise condition.

The invention further relates to an apparatus for measuring exercise condition, especially to an apparatus for measuring an exertion endurance indicator representing an exercise condition of a subject to be measured, such as maximal oxygen uptake or any such exertion endurance indicator representing physical fitness.

2. Description of the Prior Art

Condition classification representing exercise exertion based on measuring maximal oxygen uptake is used as an indicator of physical exercise condition that is, exertion endurance, for example to measure human physical performance, such as exertion endurance.

Prior art solutions for determining and measuring an exercise condition are either direct exertion measurement or indirect measurement. In direct exertion measurement, the maximal oxygen uptake ability is measured directly from respiratory gases under maximum exertion by means of a running mat or a bicycle ergometer, for example. In indirect measurement, the work performed is measured within a specific period of time, such as in so-called Cooper test where a distance run during 12 minutes is measured. In both known methods the measurement of exercise condition takes place by measuring an active performance, wherefore these methods are laborious, difficult and expensive to arrange in order to determine condition. Average resting heartbeat is considered to be one indicator of condition, but it does not give reliable results as the correlation of resting heartbeat to maximal oxygen uptake ability is only at the rate of 0.4 to 0.45. Other heartbeat parameters also do not attain better correlations to maximal oxygen uptake ability.

OBJECTS AND SUMMARY OF THE INVENTION

An object of the present invention is to provide a new method that will avoid the problems associated with prior art methods.

This object is attained in accordance with a method of the invention in which a calculation formula obtained by means of a neural network is used for measuring an exertion endurance indicator representing an exercise condition, to which formula input parameters representing the subject to be measured are supplied. Such input parameters comprise at least one or more of the following physiological parameters: sex, age, height, weight. One or more output parameters representing the exertion endurance indicator representing the fitness of the subject to be measured are obtained from the calculation formula. The neural network construction used for formulating the calculation formula is trained with a sufficiently large number of real measuring results comprising similar input parameters and one or more similar output parameters. In addition to the physiological parameters, one or more resting heartbeat parameters measured specifically from resting heartbeat are used as the input parameters of the calculation formula. Similar resting heartbeat parameters are used in the training of the neural network used in formulating the calculation formula of the exertion endurance indicator representing an exercise condition.

This object is attained in a second embodiment of the present invention using the method of the invention. In accordance with the method, physiological input parameters representing the subject to be measured are supplied to a predetermined calculation formula, the input parameters comprising at least one or more of the following physiological parameters, such as sex, age, height, weight. From the calculation formula, one or more output parameters representing the exertion endurance indicator, such as maximal oxygen uptake ability or any other such exertion endurance indicator representing the exercise condition of the subject to be measured, are obtained. In addition to the physiological parameters, one or more resting heartbeat parameters measured from resting heartbeat are used as input parameters of the calculation formula An apparatus according to the invention comprises means for detecting resting heartbeat and sending resting heartbeat data to a calculation unit. Means are provided for supplying physiological parameters representing the subject to the calculation unit. The calculation unit generates an exertion endurance signal representing an exercise condition, such as maximal oxygen uptake ability, condition classification or any such physical condition indicator based on the physiological parameters and resting heartbeat data supplied to it. A display and/or a memory are provided for indicating and/or storing the physical condition data.

The method and apparatus of the invention are based on the idea that resting heartbeat parameters are used as input data of exercise exertion endurance, and a calculation formula predetermined preferably by means of a neural network is used. Resting heartbeat parameters and human physical parameters are supplied to the formula as input data and maximal oxygen uptake (for example) is calculated as output data representing human physical condition, that is, exertion endurance. In formulating the calculation formula, the neural network, if used, would be trained by corresponding data by using an extensive real measurement material. Different parameters of a person's heartbeat and heartbeat variation measured during a few minutes are needed as measurement data and, in addition to the parameters obtained from their heartbeat, human physical measurement parameters, such as weight, height, age and sex, are utilized. The data measured from resting heartbeat and personal pre-data are provided to the calculation formula as supply data. When determining the calculation formula by a neural network, different rules have been made by means of fuzzy logic, that is, the effect of different variables or variable combinations on the end result is made fuzzy. The calculation formula determined by means of the neural network calculates by weightings obtained on the basis of training material the maximal uptake ability of a person from the new supply data and determines a corresponding condition class.

Neural networks are known per se, and they have been used previously for measuring a patient's condition of health, the seriousness of a person's infarct, the risk of death for elderly persons or a person's blood pressure. These solutions have been disclosed for example in EP-555591.

DE-4307545 further discloses an apparatus that determines the location and the extent of a person's infarct. This apparatus employs multi-channel EKG measurement, and infarct determination is based on the trained use and classification of neural network construction in the apparatus.

EP-650742 discloses an apparatus which controls a pacemaker, i.e. a defibrillator by means of a neural network. This apparatus measures the EKG curve, compares it to the data bank and decides if a pacemaker pulse is needed.

WO-92/03094 discloses an apparatus in which a patient's heart is diagnosed by means of heart sounds by using a neural network construction.

U.S. Pat. No. 5,251,626 discloses an apparatus for detecting and classifying arrhythmias which is similar to that in EP 650742 cited above.

U.S. Pat. No. 5,280,792 discloses an apparatus for detecting and classifying arrhythmias that is similar to what is disclosed in EP 650742 and U.S. Pat. No. 5,251,626 cited above.

DE-4338958 discloses an apparatus and a method for determining a person's optimal exercise heartbeat. In this solution an optimal exercise heartbeat is determined by using an iterative method where first an initial heartbeat level/load is determined by using known formulae and then heartbeat level under load is measured. The difference between assumed and measured heartbeat level is used to optimize the correct heartbeat level/load level. The result can be further specified by taking other variables and factors into account by using a neural network and/or a multi-variable analysis. The disadvantage of the solution is that heartbeat has to be measured during loading. This solution refers to a maximal oxygen uptake ability, but in this solution maximal oxygen uptake is used as input data and not as calculation output data as in the solution of the invention.

The references cited above are in no way related to measurement of exertion endurance.

The above-mentioned prior art solutions all use heartbeat measurement values measured under exertion without any more specific heartbeat data analyses, whereas according to the preferred embodiment of the solution of the invention, one or more RR interval parameters, such as mean heartbeat interval, standard deviation of heartbeat intervals or maximum heartbeat interval, are calculated from resting heartbeat.

Several advantages are attained with the method of the invention. The method of the invention is very accurate, simple, advantageous in its costs and easy to implement as a method for measuring exercise condition or exertion endurance, such as maximal oxygen uptake ability. The method of the invention is very useful for testing and determining the an exercise condition of ordinary persons who exercise because it is easy to record resting heartbeat during a few minutes, determine the physical parameters and supply them to the necessary measurement apparatus as no exertion test need be done. The new, accurate and easy method of the invention can also be used by sportsmen/sportswomen for monitoring changes in exercise condition. More accurate direct tests can be made less often as reference. The method of the invention will also save expenses, which are considerable in a direct test. By the method of the invention, a correlation at the rate of 0.97 has been obtained as a result between the maximal oxygen uptake ability calculated by the neural network based calculation formula and on the other hand, oxygen uptake ability measured with the direct method. By means of the invention, it is possible to determine a person's physical exercise condition and performance reliably and easily without maximal exertion. The method of the invention can be implemented, for example, by means of a heartrate monitor worn on a wrist, a health watch or in connection with some other such apparatus.

BRIEF DESCRIPTION OF THE DRAWINGS

In the following, the invention will be explained in more detail with reference to the accompanying drawings, wherein FIG. 3 shows one neural network construction used for determining a calculation formula of physical condition, FIG. 5 shows coefficient and bias matrices determined on the basis of the neural network construction and the extensive test material supplied thereto.

DETAILED DESCRIPTION OF THE PREFERRED EMBODIMENTS

Figure 7:
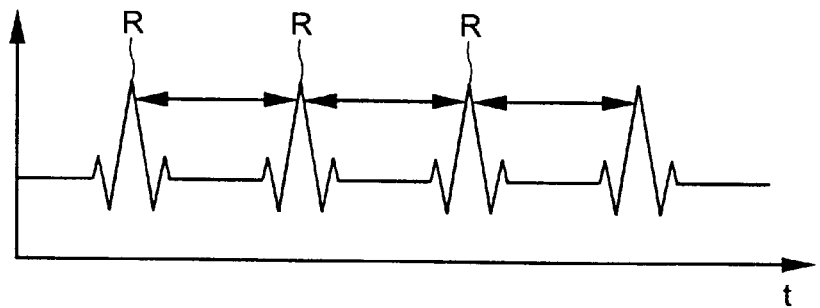
FIG. 7 shows resting heartbeat.

FIG. 7 shows a typical EKG signal caused by heartbeat. P, Q, R, S, T and U waves can be identified in each signal by accurate measuring. The R wave is formed by polarization of the ventricles of the heart and generally represents a peak value. Peak value R represents the maximum point of the EKG signal and the interval R-R represents a beat interval. The beat can be measured from a pressure pulse or optically.

Figure 6:
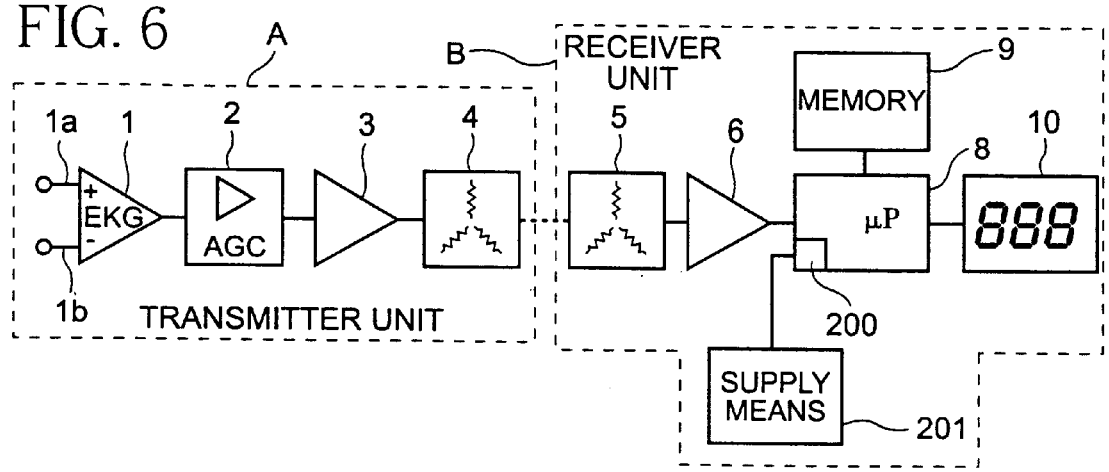
FIG. 6 shows an apparatus for applying the method according to the invention.

FIG. 6 shows an example of a heartrate monitor applied in the invention. Preferably the heartrate monitor comprises a heartbeat transmitter unit A attached to the chest of a person to be examined and a receiver unit B for receiving heartbeat signals wirelessly from the transmitter unit. Heartbeat measurement and analysis functions are included in the receiver unit. To be more specific, the exemplary equipment shown in FIG. 6 includes a transmitter unit A comprising an EKG pre-amplifier 1 to which heartbeat identifying electrodes 1a, 1b are connected. The signal of the pre-amplifier 1 is amplified in an AGC amplifier 2 and further in a power amplifier 3 where a heartbeat signal controlling windings 4 is produced, in which signal the interval between the pulses in the signal is the same as the interval of heartbeats. A magnetic field varying at the rate of the heartbeat is thus generated to the windings 4. The magnetic field provided by a transmitting coil or windings 4 is detected by a coil 5 of the receiver unit B forming the other part of the equipment. The coils 4 and 5 form an inductive coupling, which operates by means of the magnetic field, between the transmitter unit A and the receiver unit B. The received signal is amplified by means of amplifier circuits 6 and 7 in the similar way as in the transmitter. The amplified signal is conveyed to a microprocessor 8 that calculates from the heartbeat signal desired factors. A memory 9 and a display device 10 are attached to the microprocessor. In these respects the apparatus is similar to known heartrate monitors.

New features in the equipment shown in FIG. 6 include a calculation unit 200 and supply means 201. In a practical implementation the calculation unit 200 can be implemented as a program of the microprocessor. The calculation unit 200 is supplied with resting heartbeat parameters calculated on the one hand by the microprocessor 8 and on the other hand, by supply means 201. A person supplies physiological input parameters describing the person, such as sex, age, height, weight.

The invention thus relates to a method for measuring physical exercise condition, preferably human physical exercise condition, or exertion endurance of a subject to be measured. In the method a specific predetermined calculation formula is used in the calculation unit 200 to which physiological input parameters representing the subject to be measured are supplied, said input parameters comprising at least one or more of the following physiological parameters: sex, age, height, weight. From the calculation formula one or more output parameters, such as maximal oxygen uptake ability representing the condition of the subject to be measured are obtained as a result. In accordance with the invention, the method is such that in addition to physiological parameters one or more resting heartbeat parameters measured from the resting heartbeat are used as an input parameter of the calculation formula. The calculation formula may be implemented in the equipment shown in FIG. 6 by the calculation unit 200 which can be integrated as a program of the microprocessor 8 of the heartrate monitor receiver unit B.

In a preferred embodiment of the invention, the method is such that the resting heartbeat is measured during a period of a few minutes, most preferably during a period of 2 to 5 minutes. On the one hand, measurement is easy to perform, but on the other hand, it is long enough for the measurement to be reliable when information about heartbeat variation is obtained.

In a preferred embodiment, the method is such that one or more of the following resting heartbeat parameters such as mean heartbeat interval, standard deviation of heartbeat intervals, maximum mean heartbeat interval, are determined as input parameters from resting heartbeat. These parameters an be calculated in the microprocessor 8 of the receiver unit B of the heartrate monitor, for example.

In a preferred embodiment of the invention, the method is such that by combining input parameters, one or more input parameter combinations are formed. Some examined input parameters are shown in Table 1.

TABLE 1

Features, i.e. input parameters used in the method

| Feature | Explanation |
| --- | --- |
| Age | The age of a test person with an accuracy of one year |
| Sex | The sex of a test person |
| Weight | The weight of a test person with an accuracy of 0.2 kg |
| Height | The height of a test person with an accuracy of 1 cm |
| Fuzzy_1 | The value of membership function in a fuzzy set 'older persons' |
| Fuzzy_2 | The value of membership function in a set of 'non-medium weight persons' |
| Fuzzy_3 | The value of the membership function in a set 'great heartbeat intervals on the average' |
| Low_ave_3 | Averaged maximal respiration modulation to heartbeat frequency |
| PRC99 | The accumulation value (percentage) of heartbeat histogram at 99% |
| Max | Maximum heartbeat interval |
| Mean | Mean heartbeat interval |
| Sdev | Standard deviation of heartbeat intervals |

With reference to Table 1, one or more different rules are formed by means of fuzzy logic with which rules the effect of one or more input parameters and/or one or more input parameter combinations on the output parameter, that is, on maximal oxygen uptake ability representing condition is made fuzzy. The unit liter per minute (1/min) and/or milliliter per kilogram per minute (ml/kg/min) can be used as a unit of maximal oxygen uptake ability.

In a preferred embodiment of the invention with reference to FIG. 3, the method comprises preclassification and an actual calculation after it. In said preferred embodiment, the method is such that preclassification is carried out by means of one or more physiological input parameters, in which the possible solution area is searched on which the value of the output parameter to be calculated is estimated to lie, and that at the actual calculation stage, the input parameters of resting heartbeat are also used, whereby at the calculation stage, the value of the output parameter representing the physical condition of the subject to be measured is moved towards the correct value on the basis of the input parameters of resting heartbeat.

Figure 4:
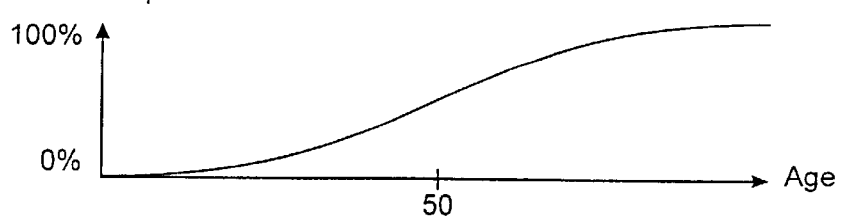
FIG. 4 shows a membership function in a fuzzy group.

In the preferred embodiment of the invention, one or more input parameters which are made fuzzy are also used in addition to the physiological input parameters. This is illustrated in FIG. 4 which shows membership function in a fuzzy set "old". FIG. 4 is a graphical representation of the concept membership function of fuzzy logic. The membership function shows at how great proportion in this example a person of a certain age belongs to the set old. Fuzzy logic represents a way of thinking where membership to a certain set is a continuous concept. A middle-aged person belongs partly to the set young and partly to the set old. By using fuzzy logic, new parameters, that is, features of heartbeat parameters and a person's weight, height, age and sex are formed to the input vector VR which can be seen in FIG. 2. The input vector VR comprises the input parameters present in Table 1.

As it concerns measurement of human physical exercise condition, that is, of exertion endurance, the method in the preferred embodiment is such that the value of maximal oxygen uptake ability corresponding to input parameters and/or condition classification representing oxygen uptake ability or any other such value representing physical exercise exertion endurance is obtained as an output parameter as a result of calculation.

In a preferred embodiment of the invention, known empirical data is used in the calculation formula, and empirical data is provided to the calculation formula according to fuzzy rules.

In a preferred embodiment of the invention, one or more of the following pieces of information are used as empirical data; "an older person is probably in a poorer condition", "the weight of a person correlates with the condition of the person best in the person set non-medium weight", "the person with a great mean heartbeat interval is probably in a good condition".

In a preferred embodiment of the invention, the method is implemented by the calculation unit 200, and the calculation unit 200 implementing this method is integrated into a heartrate monitor receiver unit mounted B to a wrist strap.

In the preferred embodiment of the invention the resting heartbeat is measured by means of measuring means 1 to 4 in connection with the receiver unit or other such apparatus. A wireless or contact coupling may be used to couple the transmitter and receiver units. The physiological input parameters, such as sex, age, height, weight, are supplied to the calculation unit 200 included in this heartrate monitor receiving unit B or any other such apparatus by means of supply means 201 in connection with the apparatus or connected to it by a wireless or contact coupling. The calculation result is shown on the display 10 and/or is stored in the memory 9 as shown in FIG. 6. In the preferred embodiment of the invention, the calculation result is shown on the display 10 included in the heartrate monitor receiver unit B or any other such apparatus. In the preferred embodiment of the invention, the heartrate monitor receiving unit or any other such apparatus is positioned on a person's wrist.

The heartrate monitor transmitter unit A and associated components 1 to 4 can be, as in FIG. 6, inductively coupled to the heartrate monitor receiver unit B, but they could also be in the case of the heartrate monitor receiver unit B, or otherwise in a wireless coupling, or in some other contact coupling to the heartrate monitor receiver unit B.

The supply means 201 of physiological input parameters, such as sex, age, height, weight, can also be in a wireless or contact coupling to the heartrate monitor receiving unit B, but they could be coupled in some other way, too. The simplest and most reliable method known to the applicant is to integrate the supply means 201 in connection with the receiver unit B of the heartrate monitor.

The neural network construction NN shown in FIG. 3 is utilized in a preferred embodiment of the invention. In that case the method according to the preferred embodiment of the invention uses a calculation formula which is obtained by means of the neural network construction NN to which input parameters representing the subject to be measured are supplied. The input parameters comprise at least one or more physiological parameters, such as sex, age, height, weight. The calculation formula provides one or more output parameters representing the exercise condition, that is, exertion endurance of a subject to be measured. The neural network construction NN used for forming the calculation formula has been trained with a sufficiently large number of real measurement results, such as clinical measurement results of 200 test subjects comprising corresponding input parameters and one or more similar output parameters as those that the calculation unit 200 uses in calculation. According to the invention, one or more resting heartbeat parameters measured from resting heartbeat are used as input parameters of the calculation formula in addition to the physiological parameters. Corresponding resting heartbeat parameters are used in training the neural network NN used for formulating the calculation formula.

The calculation matrices obtained as a result of training the neural network construction are realized as a calculation formula by using known activation functions, and multiplication and addition.

Figure 1:
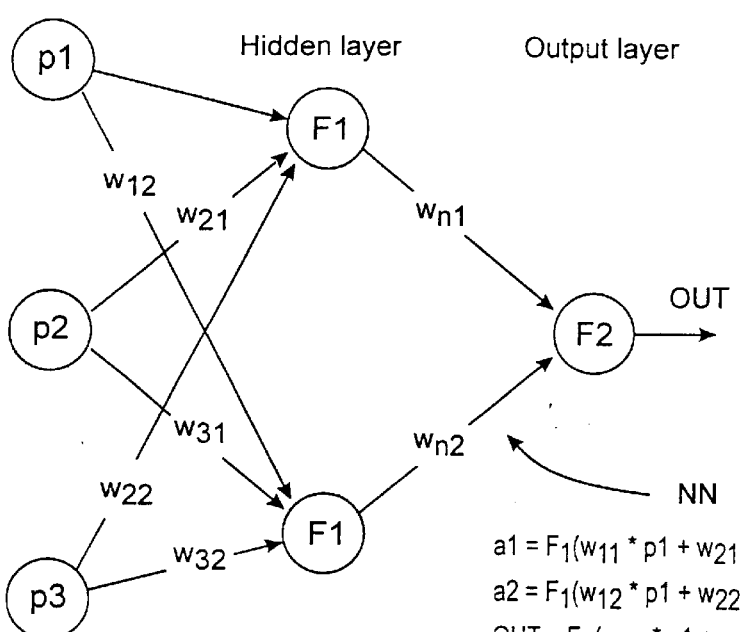
FIG. 1 shows a graphical representation of the neural network construction.
Figure 2:
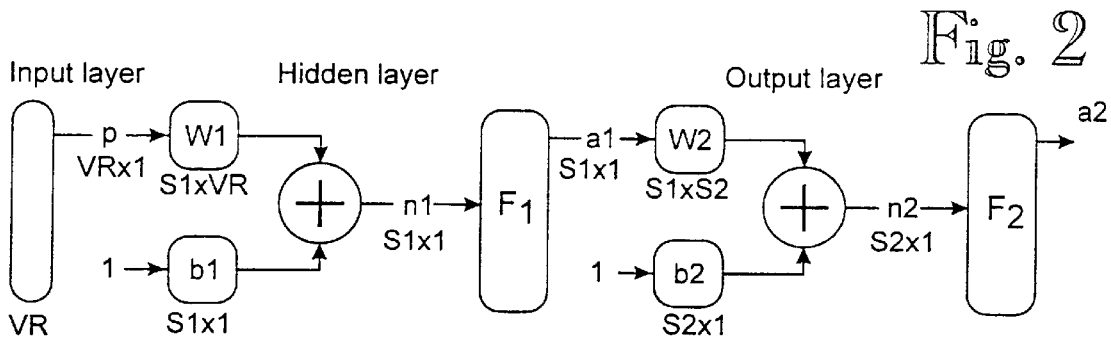
FIG. 2 shows a neural network construction in a matrix form.

With reference to FIGS. 1 to 3 in particular, the neural network NN comprises an input layer, an output layer and a hidden layer. There may be several neurons in each layer. Each cell parameter forms one input neuron in the input layer. There are as many neurons in the output layer as output variables. The number of neurons in the intermediate layer depends on the structure of the network. The signals of the neurons in the network are calculated by combining the variables and/or neurons of the previous layer using linear or non-linear activation functions.

A simple neural network construction NN is disclosed in FIG. 1. The structure includes an input layer, one hidden layer and an output layer. There are three cells in the input layer that are not neurons but illustrate values of the input vector. In the hidden layer there are two neurons to which the cells in the input layer are completely connected. The connections comprise weighting coefficients with which the strength of the signal is weighted in summing in the following layer. Each hidden layer and input layer can be associated with a bias vector which has been omitted in this presentation for the sake of simplicity. FIG. 1 also shows the algebraic formulae of the neural network example.

In FIG. 2 the neural network construction NN is shown by using matrix and vector formulae. Bias vectors b which improve the operation of the neural network construction NN are also added to the figure. The determination of the weighting coefficients of the neural network takes place by using general training algorithms of neural calculation. A coefficient matrix and a bias vector b are obtained for each neuron layer as a result of the training of the network. The neural network can after this be realized by using mathematical functions, multiplication and summing in a simple programmable form as a computer program.

It was stated earlier that preclassification and actual calculation after it are used in the method. This division is a result of the neural network construction NN of FIG. 3 used in the preferred embodiment. The neural network construction NN comprises two sections: a preclassifier and an actual calculation structure. Physiological and fuzzy features according to Table 1 are used in the preclassification. An advantage of preclassification is that the physiological features define the possible solution area, a small woman, for example, cannot have the lung capacity of a big man.

The model of the neural network NN is shown in FIG. 3 where the features shown in Table 1 are input quantities. The size of the correlation to the quantity to be measured, that is, to maximal oxygen uptake ability is examined in selecting the features.

A backpropagation method, for example, or any such suitable method has been used in the training of the neural network NN. Coefficient and bias tables in the matrix form according to FIG. 5 are obtained as a result. The matrices of the preclassifier have an identifier F and the matrices of the basic structure B. Weighting coefficient matrices are identified by w index and bias vectors by b index. The numerical index notifies the number of the layer. The indication p represents features, that is, input parameters.

The invention can be disclosed briefly in such a manner that at first a person's heartbeat at rest is measured for example in a sitting position during a few minutes. Various heartbeat and heartbeat interval parameters, such as mean heartbeat, standard deviation, maximum of successive beats and minimum intervals and/or other parameters, are calculated from the heartbeat data by means of software in the microprocessor 8, for example. These parameters are used as supply data in the calculation unit 200. Other data, such as age, sex, weight and height, obtained from the supply means 201 is also used a supply data for the calculation unit 200. By combining this data by using different rules, new parameters are derived which can further be made fuzzy by means of fuzzy logic. As an exemplary rule it could be mentioned that the condition or maximal oxygen uptake ability of a short and heavy person is probably not good.

Figure 8:
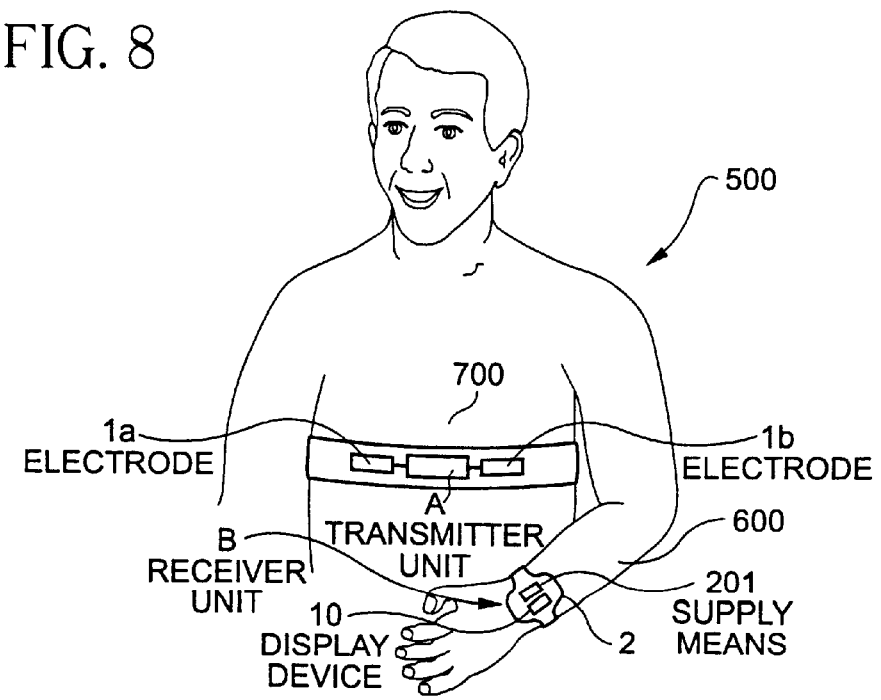
FIG. 8 shows the apparatus used by a human being.

With reference to FIGS. 6 and 8 in particular, it is stated that in addition to the method, the invention relates thus to an apparatus A, B for measuring the physical exercise condition, that is, exertion endurance, that is, performance of a subject to be measured. The apparatus comprises means 1 to 4 for detecting resting heartbeat and for sending it to the calculation unit 8, 200 included also in the apparatus. The apparatus also comprises means 201 for supplying physiological input parameters representing the subject to be measured to the calculation unit 8, 200 for calculating an output quantity representing condition, such as maximal oxygen uptake ability, condition classification or any other such indicator of physical exercise condition, on the basis of the physiological features and the heartbeat data also supplied to the calculation unit 8, 200. The apparatus also comprises means, such as a display 10 and/or a memory 9, for indicating and/or storing physical exercise condition, that is, exertion endurance obtained as a result of calculation.

In a preferred embodiment of the invention, the apparatus A, B comprises a transmitter unit A and a receiver unit B connected thereto by an inductive, optical or some other wireless telemetric coupling. The transmitter unit A comprises means 1 to 4 for detecting and sending heartbeat signals, and the receiver unit B comprises means 5 for receiving heartbeat signals from the transmitter unit A, and said calculation unit 8, 200, and said means 201 for supplying the physiological input parameters to the calculation unit 8, 200, and said means 10 for displaying and/or storing the result of calculation.

As regards an apparatus, the apparatus A, B implementing the method can be realized in may ways but the Applicant has observed that the most practical and advantageous method is as in FIG. 8 which shows a wrist strap of the heartrate monitor receiver unit B. In this case the heartrate monitor receiver unit B includes at least the calculation unit 8, 200, the supply means 201 of physiological data and the display and/or the memory. The transmitter unit A included in the apparatus has a wireless coupling to the heartrate monitor receiver unit B. The operation of the transmitter unit A can be integrated into the wrist strap of the heartrate monitor receiver unit B if the measurement of heartbeat on the wrist, for example, is reliable enough. It can be seen in FIG. 8 that the wrist strap of the heartrate monitor receiver unit B is on a wrist 600 of a human being 500, and the transmitter unit A is on the human body, particularly on a chest 700 of the human being 500 as a so-called electrode belt.

In a preferred embodiment of the invention, the apparatus, preferably the calculation unit 8, 200 comprises means 8 by which one or more of the following resting heartbeat parameters, such as mean heartbeat interval, standard deviation of heartbeat intervals, maximum heartbeat interval, are determined as input parameters from resting heartbeat.

In a preferred embodiment of the invention, the calculation unit 200 comprises a calculation formula determined by the neural network construction NN.

The preferred embodiments of the invention disclosed above and the other more detailed solutions will improve the accuracy, speed and usability of the method of the invention.

The apparatus can also be realized by using a portable, transferable or fixed computer equipment to which input parameters are supplied directly or indirectly.

Although the invention has been described above with reference to the examples illustrated in the accompanying drawings, it will be clear that the invention is not restricted thereto, but it can be modified in many ways within the inventive concept disclosed in the appended claims.

What is claimed is:

1. An apparatus for measuring an exertion endurance indicator representing an exercise condition of a subject to be measured, said apparatus comprising:

a heartbeat monitor for detecting a resting heartbeat of said subject and generating a heartbeat signal in response thereto;

means for supplying selected physiological parameters associated with said subject;

a calculation unit for generating an exertion endurance signal in response to said heartbeat signal and said physiological parameters according to a predetermined calculation formula, said calculation unit being operatively connected to said heartbeat monitor and including at least one input for receiving said physiological parameters from said means for supplying physiological parameters, said exertion endurance signal representing the exercise condition of said subject;

a neural network trained with a sufficient number of empirical measurement results comprising a plurality of physiological parameters and resting heartbeat parameters, and a plurality of corresponding exertion endurance indicators, said calculation formula being determined by said neural network; and a display operatively connected to said calculation unit for indicating the exercise condition of said subject in response to said exertion endurance signal.

2. The apparatus of claim 1, further comprising memory for storing said exercise condition of said subject.

3. The apparatus of claim 1, wherein said calculation unit and said neural network are formed as a microprocessor for running a predetermined application program.

4. The apparatus of claim 1, wherein said physiological parameters are selected from the group consisting of sex, age, height and weight.

5. The apparatus of claim 1, wherein said exertion endurance signal represents the maximal oxygen uptake ability of said subject.

6. The apparatus of claim 1, wherein said heartbeat monitor comprises:

a sensor for detecting a heartbeat signal from said subject to be measured;

a transmitter operatively connected to said sensor for wirelessly transmitting said heartbeat signal; and a receiver for wirelessly receiving said heartbeat signal from said transmitter.

7. The apparatus of claim 6, further comprising a wrist unit, wherein at least said receiver, said means for supplying physiological parameters, said calculation unit and said display are integrated with said wrist unit.

8. A method for measuring a physical exercise condition of a subject to be measured, the method comprising the steps of:

measuring a resting heartbeat of said subject and determining therefrom at least one resting heartbeat parameter;

supplying at least one physiological parameter associated with said subject to be measured;

calculating at least one exertion endurance indicator according to a predetermined calculation formula, said calculation formula using, as input parameters to said formula, said at least one resting heartbeat parameter and said at least one physiological parameter, said at least one exertion endurance indicator representing the physical condition of said subject without using any input parameters obtained from exercise performed by the subject to be measured.

9. The method of claim 8, further comprising the step of displaying said at least one exertion endurance indicator.

10. The method of claim 8, further comprising the step of storing said at least one exertion endurance indicator.

11. The method of claim 8, wherein said at least one physiological parameter is selected from the group consisting of sex, age, height and weight.

12. The method of claim 8, wherein said at least one exertion endurance signal represents the maximal oxygen uptake ability of said subject.

13. The method of claim 8, wherein said at least one resting heartbeat parameter is selected from the group consisting of mean heartbeat interval, standard deviation of heartbeat intervals, minimum mean heartbeat interval and maximum mean heartbeat interval.

14. The method of claim 8, further comprising the step of providing a calculation unit, said calculation unit generating said at least one exertion endurance indicator in response to said at least one resting heartbeat parameter and said at least one physiological parameter.

15. The method of claim 14, further comprising the step of providing a heart rate monitor, wherein said calculation unit is integrated in a portion of said heart rate monitor.

16. The method of claim 8, further comprising the step of providing a microprocessor, wherein said step of calculating at least one exertion endurance indicator is performed by a software application program running on said microprocessor.

17. A method for measuring a physical exercise condition of a subject to be measured, the method comprising the steps of:

measuring a resting heartbeat of said subject and determining therefrom at least one resting heartbeat parameter;

supplying at least one physiological parameter associated with said subject to be measured;

providing a neural network;

causing said neural network to generate a calculation formula;

calculating at least one exertion endurance indicator according to said calculation formula generated by said neural network, said calculation formula using, as input parameters to said formula, said at least one resting heartbeat parameter and said at least one physiological parameter, said at least one exertion endurance indicator representing the physical condition of said subject.

18. The method of claim 17, further comprising the step of displaying said at least one exertion endurance indicator.

19. The method of claim 17, further comprising the step of storing said at least one exertion endurance indicator.

20. The method of claim 17, wherein said at least one physiological parameter is selected from the group consisting of sex, age, height and weight.

21. The method of claim 17, wherein said at least one exertion endurance signal represents the maximal oxygen uptake ability of said subject.

22. The method of claim 17, wherein said at least one resting heartbeat parameter is selected from the group consisting of mean heartbeat interval, standard deviation of heartbeat intervals, minimum mean heartbeat interval and maximum mean heartbeat interval.

23. The method of claim 17, wherein the step of providing a neural network includes providing a neural network which has been trained with a sufficient number of empirical measurement results comprising a plurality of physiological parameters and resting heartbeat parameters, and a plurality of corresponding exertion endurance indicators.

24. The method of claim 17, wherein the step of measuring a resting heartbeat is performed during a period in the range of between two and five minutes.

25. The method of claim 17, further comprising the step of providing a microprocessor, wherein said steps of providing a neural network, causing said neural network to generate a calculation formula and calculating at least one exertion endurance indicator are performed by a software application program running on said microprocessor.

26. The method of claim 17, further comprising the steps of:

preclassifying said at least one physiological parameter associated with said subject and creating a solution range based on said at least one physiological parameter within which said at least one exertion endurance indicator value, determined from said calculating step, is predicted to lie; and adjusting said at least one exertion endurance indicator value in response to said at least one resting heartbeat parameter such that said at least one exertion endurance indicator value is within said solution range.

27. The method of claim 17, wherein said step of causing said neural network to generate a calculation formula is performed using at least one fuzzy logic rule, wherein said at least one exertion endurance indicator, determined from said calculating step, is made fuzzy.

28. An apparatus for measuring an exertion endurance indicator representing an exercise condition of a subject to be measured, said apparatus comprising:

a heartbeat monitor for detecting a resting heartbeat of said subject and generating a heartbeat signal in response thereto;

means for supplying selected physiological parameters associated with said subject;

a calculation unit for generating an exertion endurance signal in response to said heartbeat signal and said physiological parameters according to a predetermined calculation formula, said calculation unit being operatively connected to said heartbeat monitor and including at least one input for receiving said physiological parameters from said means for supplying physiological parameters, said exertion endurance signal representing the maximal oxygen uptake ability of said subject; and a display operatively connected to said calculation unit for indicating the exercise condition of said subject in response to said exertion endurance signal.

29. A method for measuring a physical exercise condition of a subject to be measured, the method comprising the steps of:

measuring a resting heartbeat of said subject and determining therefrom at least one resting heartbeat parameter;

supplying at least one physiological parameter associated with said subject to be measured;

calculating at least one exertion endurance indicator according to a predetermined calculation formula, said calculation formula using, as input parameters to said formula, said at least one resting heartbeat parameter and said at least one physiological parameter, said at least one exertion endurance indicator representing the maximal oxygen uptake ability of said subject.

* * * * *

UNITED STATES PATENT AND TRADEMARK OFFICE
CERTIFICATE OF CORRECTION

PATENT NO.    : 6,277,080 B1
DATED         : August 21, 2001
INVENTOR(S)   : Nissilä et al.

Page 1 of 1

It is certified that error appears in the above-identified patent and that said Letters Patent is hereby corrected as shown below:

<u>Title page,</u>
Now reads "[73]: Assignee: Polar Electro Oy, Kemple (FI)"; should read -- [73]: Assignee: Polar Electro Oy, Kempele (FI) --; and should read -- [30] Foreign Application Priority Data Mar. 12, 1996 [FI] Finland.................. 961148 --.

Signed and Sealed this

Second Day of April, 2002

Attest:

JAMES E. ROGAN
Attesting Officer    *Director of the United States Patent and Trademark Office*